US010206867B2

(12) United States Patent
Holderith et al.

(10) Patent No.: US 10,206,867 B2
(45) Date of Patent: Feb. 19, 2019

(54) **ALCOHOLIC EXTRACT OF AERIAL PARTS OF *SOLIDAGO VIRGAUREA* SUBSP. *ALPESTRIS*, METHOD OF PRODUCTION THEREOF, AND COSMETIC OR DERMATOLOGICAL COMPOSITION CONTAINING IT**

(71) Applicants: CHANEL PARFUMS BEAUTE, Neuilly sur Seine (FR); CENTRE NATIONAL DE LA RECHERCHE SCIENTIFIQUE—CNRS, Paris (FR); Universite de Nice Sophia Antipolis, Nice (FR)

(72) Inventors: Serge Holderith, Vincennes (FR); Anais Tromeur, Paris (FR); Irina Berlin, Vincennes (FR); Xavier Fernandez, Nice (FR); Alexandre Casale, Nice (FR); Johannes Grillari, Bisamberg (AT); Ingo Lammermann, Vienna (AT); Florian Gruber, Vienna (AT); Marie-Sophie Narzt, Vienna (AT); Gaëlle Gendronneau, Pantin (FR)

(73) Assignees: CHANEL PARFUMS BEAUTE, Neuilly sur Seine (FR); CENTRE NATIONAL DE LA RECHERCHE SCIENTIFIQUE—CNRS, Paris (FR); UNIVERSITE DE NICE SOPHIA ANTIPOLIS, Nice (FR)

( * ) Notice: Subject to any disclaimer, the term of this patent is extended or adjusted under 35 U.S.C. 154(b) by 0 days.

(21) Appl. No.: 15/361,176

(22) Filed: Nov. 25, 2016

(65) Prior Publication Data

US 2017/0151170 A1    Jun. 1, 2017

(30) Foreign Application Priority Data

Nov. 26, 2015 (FR) ...................... 15 61400

(51) Int. Cl.
*A61K 36/28* (2006.01)
*A61K 8/97* (2017.01)
*A61Q 19/02* (2006.01)
*A61Q 19/08* (2006.01)
*A61K 8/9789* (2017.01)

(52) U.S. Cl.
CPC .............. *A61K 8/97* (2013.01); *A61K 8/9789* (2017.08); *A61K 36/28* (2013.01); *A61Q 19/02* (2013.01); *A61Q 19/08* (2013.01); *A61K 2236/333* (2013.01); *A61K 2236/37* (2013.01); *A61K 2800/522* (2013.01); *A61K 2800/78* (2013.01)

(58) Field of Classification Search
None
See application file for complete search history.

(56) References Cited

U.S. PATENT DOCUMENTS

2009/0004302 A1    1/2009  Cyr
2009/0214677 A1*   8/2009  Literati Nagy ........ A61K 36/28
                                                     424/725

FOREIGN PATENT DOCUMENTS

WO        2010072923         7/2010
WO     WO-2010072923 A1 *    7/2010  ............... A61K 8/97

OTHER PUBLICATIONS

Laurencon, et al. (2013) Phytochemistry 86: 103-111. (Year: 2013).*
Chevalier et al. (2012) Journal of Medical Microbiology 61: 1016-1022. (Year: 2012).*
Chevalier et al., "Inhibition of Candida albicans yeast-hyphal transition and biofilm formation by Solidago virgaurea water extracts", Journal of Medical Microbiology (2012) 61, 1016-1022.
Lucas Meyer Cosmetics, XP-002758558, (2014) https://web.archive.org/web/20140709015925/http://lucasmeyercosmetics.

* cited by examiner

*Primary Examiner* — Christopher R Tate
*Assistant Examiner* — Russell G Fiebig
(74) *Attorney, Agent, or Firm* — Young & Thompson

(57) ABSTRACT

An alcoholic extract of aerial parts of *Solidago virgaurea* subsp. *alpestris*, the method of production thereof, a cosmetic or dermatological composition containing it, as well as cosmetic and dermatological uses thereof, notably in the treatment of signs of skin ageing.

7 Claims, No Drawings
Specification includes a Sequence Listing.

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: primer forward TGM2

<400> SEQUENCE: 1
ggcgaaccac ctgaacaaac                                              20

<210> SEQ ID NO 2
<211> LENGTH: 20
<212> TYPE: DNA
<213> ORGANISM: Artificial Sequence
<220> FEATURE:
<223> OTHER INFORMATION: primer reverse TGM2

<400> SEQUENCE: 2
aggatgcaaa gaggaacgct                                              20

<210> SEQ ID NO 3
<211> LENGTH: 20
<212> TYPE: DNA
<213> ORGANISM: Artificial Sequence
<220> FEATURE:
<223> OTHER INFORMATION: primer forward PDPN

<400> SEQUENCE: 3
gcatcgagga tctgccaact                                              20

<210> SEQ ID NO 4
```

```
<211> LENGTH: 20
<212> TYPE: DNA
<213> ORGANISM: Artificial Sequence
<220> FEATURE:
<223> OTHER INFORMATION: primer reverse PDPN

<400> SEQUENCE: 4
cccttcagct ctttagggcg                                             20

<210> SEQ ID NO 5
<211> LENGTH: 20
<212> TYPE: DNA
<213> ORGANISM: Artificial Sequence
<220> FEATURE:
<223> OTHER INFORMATION: primer forward GAPDH

<400> SEQUENCE: 5
cgaccacttt gtcaagctca                                             20

<210> SEQ ID NO 6
<211> LENGTH: 20
<212> TYPE: DNA
<213> ORGANISM: Artificial Sequence
<220> FEATURE:
<223> OTHER INFORMATION: primer reverse GAPDH

<400> SEQUENCE: 6
tgtgaggagg ggagattcag                                             20

<210> SEQ ID NO 7
<211> LENGTH: 24
<212> TYPE: DNA
<213> ORGANISM: Artificial Sequence
<220> FEATURE:
<223> OTHER INFORMATION: primer forward CDKN1A

<400> SEQUENCE: 7
ggcggcagac cagcatgaca gatt                                        24

<210> SEQ ID NO 8
<211> LENGTH: 20
<212> TYPE: DNA
<213> ORGANISM: Artificial Sequence
<220> FEATURE:
<223> OTHER INFORMATION: primer reverse CDKN1A

<400> SEQUENCE: 8 gcaggggggcg gccagggtat                                            20

<210> SEQ ID NO 9
<211> LENGTH: 19
<212> TYPE: DNA
<213> ORGANISM: Artificial Sequence
<220> FEATURE:
<223> OTHER INFORMATION: primer forward PRPF19

<400> SEQUENCE: 9
aaccacggag cgcaagaag                                              19

<210> SEQ ID NO 10
<211> LENGTH: 19
<212> TYPE: DNA
<213> ORGANISM: Artificial Sequence
<220> FEATURE:
<223> OTHER INFORMATION: primer reverse PRPF19

<400> SEQUENCE: 10
```
cgggggaagc agaaaacac                                                        19

<210> SEQ ID NO 11
<211> LENGTH: 20
<212> TYPE: DNA
<213> ORGANISM: Artificial Sequence
<220> FEATURE:
<223> OTHER INFORMATION: primer forward B2M

<400> SEQUENCE: 11
atgagtatgc ctgccgtgtg                                                       20

<210> SEQ ID NO 12
<211> LENGTH: 19
<212> TYPE: DNA
<213> ORGANISM: Artificial Sequence
<220> FEATURE:
<223> OTHER INFORMATION: primer reverse B2M

<400> SEQUENCE: 12
caatccaaat gcggcatct                                                        19

<210> SEQ ID NO 13
<211> LENGTH: 20
<212> TYPE: DNA
<213> ORGANISM: Artificial Sequence
<220> FEATURE:
<223> OTHER INFORMATION: primer forward p16ink4A

<400> SEQUENCE: 13
caacgcaccg aatagttacg                                                       20

<210> SEQ ID NO 14
<211> LENGTH: 18
<212> TYPE: DNA
<213> ORGANISM: Artificial Sequence
<220> FEATURE:
<223> OTHER INFORMATION: primer reverse p16ink4A

<400> SEQUENCE: 14
accagcgtgt ccaggaag                                                         18

<210> SEQ ID NO 15
<211> LENGTH: 20
<212> TYPE: DNA
<213> ORGANISM: Artificial Sequence
<220> FEATURE:
<223> OTHER INFORMATION: primer forward MMP1_524

<400> SEQUENCE: 15
ggtctctgag ggtcaagcag                                                       20

<210> SEQ ID NO 16
<211> LENGTH: 20
<212> TYPE: DNA
<213> ORGANISM: Artificial Sequence
<220> FEATURE:
<223> OTHER INFORMATION: primer reverse MMP1_720

<400> SEQUENCE: 16
ccgcaacacg atgtaagttg                                                       20

ALCOHOLIC EXTRACT OF AERIAL PARTS OF *SOLIDAGO VIRGAUREA* SUBSP. *ALPESTRIS*, METHOD OF PRODUCTION THEREOF, AND COSMETIC OR DERMATOLOGICAL COMPOSITION CONTAINING IT

FIELD OF THE INVENTION

The invention relates to an extract of aerial parts of *Solidago virgaurea* subsp. *alpestris*, the method of production thereof, a cosmetic or dermatological composition containing it, as well as various cosmetic uses.

BACKGROUND OF THE INVENTION

The skin consists mainly of three layers, namely, starting from that closest to the surface, epidermis, dermis and hypodermis.

The epidermis makes an important contribution to protection of the skin and maintaining its proper function.

Ageing and photo-ageing of the skin and the associated changes may be manifested in various ways, among which we may mention:
  loss of firmness and elasticity owing to tissue loss at the level of the epidermis and/or dermis;
  loss of radiance owing to reduction of the microcirculation and slowing of cellular renewal at the level of the epidermis;
  appearance of pigmented spots; and/or
  dry skin resulting from a decline in the barrier function of the stratum corneum and slowing of epidermal renewal.

There is therefore a need to provide a polyfunctional active agent that can act on a set of causes of changes to the skin due to ageing and/or a change in the physiological mechanisms connected with ageing.

Now, the applicant has found that an alcoholic extract of aerial parts of *Solidago virgaurea* subsp. *alpestris*, obtained by a particular method, displays, through stimulation or inhibition of physiological mechanisms, interesting effects with respect to skin ageing, and the pigmentation and microcirculation of the skin. In fact, as demonstrated with examples, the alcoholic extract of aerial parts of *Solidago virgaurea* subsp. *alpestris* according to the invention has interesting cosmetic properties: it is able to combat ageing of the skin, notably through its anti-MMP3 and anti-MMP9 effects; it has antioxidant properties; it activates the microcirculation in the skin; and it has a depigmenting action. The extract according to the invention also has an anti-ageing effect on the skin, as it can delay replicative senescence, it prevents the transition of papillary fibroblasts into reticular fibroblasts, and reduces the expression of senescence markers.

Therefore, according to a first aspect, the invention relates to an alcoholic extract of aerial parts of *Solidago virgaurea* subsp. *alpestris*, obtainable by a method comprising the following steps:
  a) extracting the aerial parts of *Solidago virgaurea* subsp. *alpestris*, with at least one alcoholic solvent;
  b) incubating the mixture obtained in a) for at least 10 h;
  c) filtering the incubated mixture obtained in b); and
  d) removing the solvent from the filtrate obtained, and then final dilution in another alcoholic solvent.
Thus, in the present application, such an extract is called extract according to the invention.

SUMMARY OF THE INVENTION

The invention also relates to a method for extracting aerial parts of *Solidago virgaurea* subsp. *alpestris*, comprising the following steps:
  a) extracting the aerial parts of *Solidago virgaurea* subsp. *alpestris*, with at least one alcoholic solvent;
  b) incubating the mixture obtained in a) for at least 10 h;
  c) filtering the incubated mixture obtained in b); and
  d) removing the solvent from the filtrate obtained, and then final dilution in another alcoholic solvent.

The invention also relates to a cosmetic or dermatological composition comprising, in a cosmetically or pharmaceutically acceptable vehicle, an alcoholic extract of aerial parts of *Solidago virgaurea* subsp. *alpestris*, according to the invention. "Cosmetically or pharmaceutically acceptable vehicle" means a medium compatible with the skin, the mucosae and the appendages. Preferably, the cosmetic or dermatological composition according to the invention is suitable for application by the topical route.

The method for obtaining the extract according to the invention thus comprises the following steps:
  a) extracting the aerial parts of *Solidago virgaurea* subsp. *alpestris*, with at least one alcoholic solvent;
  b) incubating the mixture obtained in a) for at least 10 h;
  c) filtering the incubated mixture obtained in b); and
  d) removing the solvent from the filtrate obtained, and then final dilution in another alcoholic solvent.

The raw material employed consists of the aerial parts of *Solidago virgaurea* subsp. *alpestris*.

*Solidago virgaurea* subsp. *alpestris* is a plant with yellow flowers in the Asteraceae family, which notably occurs in the Provence Alpes Côte d'Azur region. The genus Solidago forms part of the Asteraceae family. It comprises from 156 to 377 species, including the species *Solidago virgaurea* L, commonly called solidago, goldenrod, or golden rod. The subspecies *Solidago virgaurea* subsp. *alpestris*, (Waldst. & Kit.) Gremli, called Small Solidago, Small Goldenrod, or Alpine Goldenrod, has the synonym *Solidago alpestris* Waldst. & Kit.

It is a hardy herbaceous plant, with straight purplish flower stems. The leaves are more or less covered with hairs, and are simple, alternating, oval and lanceolate, with a jagged edge. The yellow flowers are aggregated in capitula having 6 to 12 flowers, arranged in their turn in a cluster. Flowering takes place from July to September. The fruits are yellowish cylindrical achenes.

The subspecies *alpestris* differs from the main species *Solidago virgaurea* by its small size (5 to 30 cm instead of 1 m), small number of capitula, which moreover are a little larger, and by the fact that it grows at higher altitude. The subspecies *Solidago virgaurea* subsp. *alpestris*, appears at the end of the season in scree and stony slopes. It grows at an altitude between 1400 and 2800 meters in the mountainous regions of Northern Europe.

There are other subspecies, different from the subspecies of interest according to the invention. Notably, there is *Solidago virgaurea* subsp. *asiatica* Kitam. ex Hara, which has the synonyms *Solidago japonica* var. *japonica* and *Solidago japonica* Kitam. This subspecies *Solidago virgaurea* subsp. *alpestris*, Kitam. ex Hara measures 35 to 85 cm and flowers from August to November. It is distributed in Japan, Korea, Russia, China and the Philippines.

The aerial parts of *Solidago virgaurea* subsp. *alpestris*, used according to the invention are typically selected from the flowers, leaves, stems and mixtures thereof. Preferably, the aerial parts used are a mixture of flowers, leaves and stems of *Solidago virgaurea* subsp. *alpestris*. Preferably, these aerial parts are first dried, then ground or comminuted in the usual way.

In step a), the aerial parts are submitted to extraction with one or more alcoholic solvents, for example selected from:
$C_1$-$C_4$ monohydric alcohols, for example methanol, ethanol or isopropanol; and
diols, for example propylene glycol, 1,3-propanediol or dipropylene glycol.

Preferably, the alcoholic solvent is a monohydric alcohol comprising from 2 to 4 carbon atoms, more preferably ethanol.

Extraction is generally carried out by immersing or gently stirring the aerial parts in one or more of the aforementioned solvents at temperatures for example in the range from room temperature to 80° C., for about 30 minutes to 8 h. Preferably, the extraction in step a) is carried out for a length of time between 2 and 6 hours, at a temperature between 40° C. and 60° C.

The mixture obtained in step a) is then incubated for at least 10 h: this is step b). Preferably, the incubation in step b) is carried out for a length of time between 12 h and 30 h, at a temperature between 2° C. and 10° C. More preferably, incubation is carried out for 12 h to 15 h, at a temperature of about 4° C.

The incubated mixture obtained at the end of step b) is then filtered to remove the insoluble substances: this is step c). Preferably, filtering the extract obtained in b) is carried out on a 100-μm membrane. This gives a liquid filtrate.

Finally, the solvent present in the liquid filtrate is removed, and then the filtrate residue is diluted in another alcoholic solvent: this is step d). The alcoholic solvent used in step d) is called "another alcoholic solvent", because it is different from the alcoholic solvent used in step a). Taking this limitation into account, the alcoholic solvent is typically selected from the same group as in step a), i.e. from the $C_1$-$C_4$ monohydric alcohols and the diols.

Preferably, removal of the solvent in step d) takes place by evaporation. Preferably, final dilution is in a diol, preferably 1,3-propanediol.

Preferably, a step of bleaching the filtrate obtained in c) is added between steps c) and d). Bleaching may be effected by adsorption of the pigments present in the filtrate on activated charcoal. This bleaching step may be followed by a step of filtration of the decoloured filtrate obtained, notably on a 20-μm membrane.

Preferably, the alcoholic extract of aerial parts of *Solidago virgaurea* subsp. *alpestris* according to the invention can be obtained by a method comprising the following steps:
a) extracting a mixture of flowers, leaves and stems of *Solidago virgaurea* subsp. *alpestris*, previously dried and ground, with ethanol, at a temperature between 40° C. and 60° C. for 2 h to 5 h;
b) incubating the mixture obtained in a) for at least 12 h at a temperature between 2° C. and 6° C.;
c) filtering the incubated mixture obtained in b), to obtain a filtrate;
 bleaching the filtrate obtained in c) by adsorption on activated charcoal; then
 filtering the decoloured filtrate on a 20-μm membrane; and
d) removing the ethanol from the filtrate obtained by evaporation, and then final dilution in 1,3-propanediol.

Advantageously, the extract employed according to the invention is of a clear colour.

Moreover, said extract is in a sufficiently concentrated form to be usable without leading to the formulation problems usually encountered at the concentrations necessary for obtaining activity in cosmetic or dermatological compositions in the form of emulsion, and without having a dark colour, in contrast to the vegetable extracts obtained by usual methods, when they are in concentrated form.

Accordingly, the extract according to the invention may be used directly for preparing a cosmetic or dermatological composition.

According to a further aspect, the invention relates to the cosmetic use of an alcoholic extract of aerial parts of *Solidago virgaurea* subsp. *alpestris* according to the invention, as antioxidant, and/or depigmenting agent, and/or agent for improving the microcirculation in the skin, and/or for preventing and/or attenuating changes to the skin due to ageing.

In fact it was found, advantageously, that the alcoholic extract of aerial parts of *Solidago virgaurea* subsp. *alpestris* according to the invention has several activities of interest with respect to preventive or restorative physiological mechanisms associated with changes to the skin, notably due to ageing.

The invention therefore relates more particularly to the cosmetic use of an alcoholic extract of aerial parts of *Solidago virgaurea* subsp. *alpestris* according to the invention as an agent for inhibiting the synthesis of melanin.

It was also found that, advantageously, the alcoholic extract of aerial parts of *Solidago virgaurea* subsp. *alpestris*, according to the invention has an advantageous activity with respect to the secretion of VEGF and cytokine IL1α by the keratinocytes. In the skin, VEGF, or vascular endothelial growth factor, is a major factor in cutaneous angiogenesis. The epidermis is an important source of VEGF, secreted in large quantities by proliferating keratinocytes. The mRNA of VEGF is expressed by the normal keratinocytes, both in tissue in situ and in cell culture. It has been shown that VEGF maintains homeostasis of the endothelial cells and their ability to respond to angiogenic stimulation, even in the elderly (Watanabe Y. et al., 1997, Oncogene 14:2025-2032). Moreover, a decrease in VEGF was observed following exposure to UV radiation (Photochem. Photobiol., 1999; 70(4):674-9).

The invention also relates to the use of an alcoholic extract of aerial parts of *Solidago virgaurea* subsp. *alpestris* according to the invention as an agent for activating the secretion of VEGF and/or as an agent for inhibiting the secretion of IL1α by the keratinocytes.

The invention also relates more particularly to the cosmetic use of an alcoholic extract of aerial parts of *Solidago virgaurea* subsp. *alpestris* according to the invention for preventing and/or attenuating changes to the skin due to ageing, notably by its inhibitory action on the metalloproteinases, notably MMP3 and MMP9. The alcoholic extract of aerial parts of *Solidago virgaurea* subsp. *alpestris* according to the invention may therefore be used as an agent for inhibiting the activity of the matrix metalloproteinases (MMPs). The matrix metalloproteinases are enzymes that degrade the extracellular matrix in the context of physiological remodelling of the skin, but age and exposure to UV radiation have the effect of increasing the activity of specific MMPs, notably MMP3 and MMP9. Accordingly, there is increased degradation of the extracellular matrix, resulting in sagging of the tissues of the skin and formation of wrinkles (Ageing Res. Rev., 2002, 1(4):705-20; J. Invest. Dermatol, 2001, 117(5):1218-24).

According to a further aspect, the invention also relates to a cosmetic or dermatological composition comprising, in a cosmetically or pharmaceutically acceptable vehicle, an alcoholic extract of aerial parts of *Solidago virgaurea* subsp. *alpestris* according to the invention. Preferably, said extract is present in the cosmetic or dermatological composition at a rate from 0.001 to 10% of the total weight of the composition, in particular at a rate from 0.01 to 10%, preferably from 0.1 to 10% of the total weight of the composition. Said cosmetic or dermatological composition may notably be suitable for application by the topical route.

Advantageously, said cosmetic or dermatological composition may be in the form of a powder, an emulsion, a microemulsion, a nanoemulsion, a suspension, a solution, a lotion, a cream, an aqueous or aqueous alcoholic gel, a mousse, a serum, a solution or a dispersion for aerosols, or a dispersion of lipid vesicles.

In the case of an emulsion, it may be a water-in-oil or oil-in-water emulsion.

The cosmetic or dermatological composition according to the invention may also comprise a solvent selected as a function of the various ingredients and the method of administration.

As examples, we may mention water (preferably demineralized water), an alcohol such as ethanol, or a diethylene glycol ether such as ethoxydiglycol or diethylene glycol monomethyl ether.

Said cosmetic composition may also comprise at least one additive that is usual in this field, for example at least one compound selected from an emollient or humectant, a gelling agent and/or thickener, a surfactant, an oil, an active agent, a dye, a preservative, an antioxidant, an active agent, an organic or inorganic powder, a sunscreen and a perfume.

Notably, said composition may contain:

One or more emollient(s) or humectant(s), which may be selected for example from glycerin, the glycols, the water-soluble silicones such as that sold under the name KF6011 (Shin Etsu) and water-soluble jojoba, such as that sold under the name *Resplanta jojoba* (Res pharma).

Said emollient or humectant may be present in the composition at a content of the order of 0 to 30 wt %, preferably 2 to 10 wt %, relative to the total weight of the composition.

One or more gelling agents(s) and/or thickener(s) of the aqueous phase, selected for example from cellulose derivatives, gums of vegetable origin (guar, carob, alginates, carrageenans, pectin), of microbial origin (xanthan), clays (Laponite), the materials identified by the INCI names "ammonium acryloyldimethyltaurate/vp copolymer" and "ammonium acryloyldimethyl-taurate/beheneth-25 methacrylate copolymer" (for example those sold under the names Aristoflex AVC and HMB by Clariant).

Said gelling agent and/or thickener may be present in the composition at a content of the order of 0 to 10 wt %, relative to the total weight of the composition.

One or more surfactant(s), preferably non-ionic, present at a content of the order of 0 to 8%, preferably 0.5 to 3 wt %, relative to the total weight of the composition.

One or more fats that are liquid at room temperature, commonly called oil(s), volatile or non-volatile, hydrocarbon-containing or silicone-containing, linear, cyclic or branched, for example isododecane, cyclopentadimethylsiloxane, the dimethicones, isononyl isononanoate or pentaerythrityl tetraisostearate, preferably at a rate from 0 to about 10 wt %, preferably 0.5 to 5 wt %, relative to the total weight of the composition.

One or more active agent(s), of natural or synthetic origin, having biological activity, for example selected from vitamins, trace elements, allantoin, vegetable proteins and vegetable extracts.

One or more water-soluble dye(s) such as, for example, the disodium salt of ponceau, the disodium salt of alizarin green, quinoline yellow, trisodium salt of amaranth, disodium salt of tartrazine, monosodium salt of rhodamine, disodium salt of fuchsine or xanthophyll, preferably at a rate from 0 to about 2 wt %, relative to the total weight of the composition.

Other additives usually employed in cosmetics may also be present in the composition according to the invention, notably preservatives, antioxidants or perfumes well known in this field of technology.

A person skilled in the art is capable of selecting, from all these possible additives, both the nature and the amount of those that will be added to the composition, in such a way that the latter retains all of its properties.

The invention is illustrated by but is not limited to the following examples.

EXAMPLE 1

Preparation of an Alcoholic Extract of Aerial Parts of *Solidago virgaurea* subsp. *alpestris*, According to the Invention An alcoholic extract of aerial parts of Solidago virgaurea subsp. alpestris according to the invention is prepared by a method comprising the following steps:

a) extracting the dried and ground aerial parts (flowers, leaves and stems) of *Solidago virgaurea* subsp. *alpestris* with ethanol at a temperature of 50° C. for 3 hours;

b) incubating the mixture obtained in a) overnight at 4° C.;

c) filtering the extract obtained in b) on a 100-µm membrane;

bleaching the liquid filtrate obtained in c) by adsorption of the pigments on activated charcoal (present in an amount equal to 2% of the dried plant); then filtering the decoloured filtrate on a 20-µm membrane;

d) removing the ethanol by evaporation, and then final dilution in 1,3-propanediol (90% of solvent).

The extract thus obtained is called "Goldenrod" in examples 2 to 6 below.

EXAMPLE 2

Test for Cytotoxicity of Goldenrod in Normal Human Keratinocytes and Melanocytes Protocol:

Normal human epidermal keratinocytes and melanocytes (PromoCell) obtained from young donors were cultured in 96-well plates for 24 hours in a supplemented culture medium (respectively media KGM2 and MGM2+SupplementMix, PromoCell) at 37° C., 5% $CO_2$ The cells were then incubated with different concentrations of Goldenrod in the basic media (without supplement) for 24 hours (keratinocytes) or in the supplemented media for 5 days (melanocytes). Cytotoxicity was evaluated by means of the Cell Titer96 Aqueous One Solution Cell Proliferation Assay (Promega), based on the capacity of the viable cells to reduce the colourless/yellow tetrazolium salts to a formazan derivative with a deep brown colour. The cells were incubated with tetrazolium at 37° C. for 30 minutes and the absorbance of the formazan formed was read at 490 nm.

Results:

The cytotoxicity of Goldenrod was evaluated at different concentrations between 0.1 and 0.0125% (Table 1 below).

TABLE 1

| CELLS | Sample | | % Control |
|---|---|---|---|
| Keratinocytes | Untreated control | | 100 ± 4.4 |
| | Goldenrod | 0.1% | 105.3 ± 8 |
| | | 0.05% | 119.2 ± 2.4 |
| | | 0.025% | 127.5 ± 3.9 |
| | | 0.0125% | 120.8 ± 13.7 |
| Melanocytes | Goldenrod | 0.1% | 40.5 ± 2.2 |
| | | 0.05% | 115.6 ± 3.1 |
| | | 0.025% | 108.8 ± 2.2 |
| | | 0.0125% | 105.3 ± 4.3 |

All the determinations were repeated 5 times and the mean values were determined. The antioxidant capacity of the ingredient is expressed as the percentage reduction of the luminescence peak of Pholasin observed during the assay in the presence and in the absence of the active ingredient ±SD, with the untreated control represented at 0%.

Results:

The results obtained are presented in Table 2 below.

At all the concentrations tested, Goldenrod has considerable antioxidant activity against hydroxyl radicals, halogenated radicals and peroxynitrites, comparable to that of the highest concentration tested of the compounds used as positive controls. A dose-dependent decrease in the percentage activity of capture of superoxides was observed with decrease in the concentration of Goldenrod.

TABLE 2

| Sample | | Mean % inhibition | Sample | | Mean % inhibition |
|---|---|---|---|---|---|
| Hydroxyl radicals | | | Halogenated radicals | | |
| Untreated control | | 0 ± 4.4 | Untreated control | | 0 ± 1.85 |
| Goldenrod | 0.1% | 98.8 ± 0.1 | Goldenrod | 0.1% | 99.6 ± 0.02 |
| | 0.05% | 97.2 ± 0.3 | | 0.05% | 98.9 ± 0.05 |
| | 0.025% | 94.3 ± 0.1 | | 0.025% | 96.9 ± 0.04 |
| | 0.0125% | 89.8 ± 0.03 | | 0.0125% | 92.8 ± 0.89 |
| D-Mannitol (mM) | 6 | 95.1 ± 0.3 | Albumin (mg/ml) | 1.25 | 93.9 ± 0.69 |
| | 4 | 92.6 ± 4.7 | | 1 | 92.1 ± 3.3 |
| | 2 | 82.6 ± 14.8 | | 0.75 | 88.5 ± 5.7 |
| | 1 | 76.1 ± 14 | | 0.5 | 82.3 ± 8.9 |
| | 0.8 | 59.9 ± 3.6 | | 0.25 | 64.9 ± 13.9 |
| Peroxynitrites | | | Superoxides | | |
| Untreated control | | 0 ± 15.3 | Untreated control | | 0 ± 4.5 |
| Goldenrod | 0.1% | 115.9 ± 0.7 | Goldenrod | 0.1% | 77.7 ± 1 |
| | 0.05% | 118.3 ± 0.1 | | 0.05% | 54.8 ± 0, |
| | 0.025% | 115.7 ± 0.8 | | 0.025% | 32.1 ± 2 |
| | 0.0125% | 103.1 ± 0.3 | | 0.0125% | 32.3 ± 2.9 |
| Vitamin E Analogue (µmol/L) | 5 | 43.9 ± 0 | L-ascorbic acid (µmol/L) | 80 | 82.4 ± 1.8 |
| | 3.125 | 28.4 ± 1.2 | | 60 | 75.3 ± 1 |
| | 1.875 | 14.5 ± 4.4 | | 40 | 64.8 ± 0.8 |
| | 1.25 | 10 ± 0 | | 20 | 43.9 ± 1.4 |
| | 0.625 | 9.2 ± 0 | | 10 | 26.4 ± 3.5 |

Goldenrod is non-toxic to keratinocytes at all the concentrations tested, whereas it is toxic to melanocytes at 0.1%.

EXAMPLE 3

Evaluation of the Antioxidant Activity of Goldenrod

Protocol:

To determine the capacity of Goldenrod for trapping free radicals (hydroxyls, halogenated derivatives, peroxynitrites and superoxide radicals), i.e. its antioxidant capacity, chemiluminescence tests dependent on pholasin ABEL®1 were used (Knight Scientific Limited) according to the manufacturer's instructions. Briefly, various concentrations of ingredients were incubated with pholasin, a well known photoprotein that emits light when it binds to free radicals. D-Mannitol, albumin, vitamin E and L-ascorbic acid were used as positive controls for determining the capacity of the extract for trapping hydroxyl radicals, halogenated derivatives, peroxynitrites and superoxides, respectively.

EXAMPLE 4

Determination of the Effect of Goldenrod on the Activity of Metalloproteinases 3 and 9 of the Extracellular Matrix by Fluorometric Assay Protocol:

To evaluate the effect of Goldenrod on the activity of MMP3 and MMP9, the enzymes (Biomol SE-109 and SE-244, respectively) were incubated with different concentrations of Goldenrod, each concentration in quintuplicate. The enzymatic reaction was induced by adding the fluorescent substrate specific to each MMP enzyme, dissolved in DMSO (Bachem H-2300, M-2055). The enzymatic reaction was monitored by spectrophotometry for one hour and the fluorescence was measured after excitation/emission at wavelengths of 360/460 nm for MMP3, or 320/405 nm for MMP9. The results are expressed as the mean of the replicates ±SD and are shown in perrcentage activity of the MMPs relative to the untreated control, which represents 100%. As control, EDTA was used for inhibiting the activity of the MMPs.

Results:

The MMP enzymes are known to be involved in the degradation of the extracellular matrix, and therefore have an age-related effect on the mechanical properties of the skin.

The inventors thus determined the capacity of Goldenrod for inhibiting the activities of MMP3 and MMP9.

The data presented in Table 3 show that Goldenrod inhibits both the activity of MMP3 and of MMP9 at the highest concentration tested of 0.1%.

These results show that Goldenrod may limit the degradation of the extracellular matrix and thus preserve the dermal integrity of the skin.

TABLE 3

| Sample | | Enzyme activity | |
|---|---|---|---|
| | | MMP3 | MMP9 |
| Untreated control | | 100 ± 7.8 | 100 ± 2.2 |
| Goldenrod | 0.1% | 40 ± 3.7 | 60 ± 9.5 |
| EDTA | 5 mM | 4.3 ± 5.3 | 0 ± 0.9 |

EXAMPLE 5

Evaluation of the Effect of Goldenrod on the Secretion of Vegf and IL1α by the Normal Human Keratinocytes in Culture by the Elisa Assay Protocol:

The keratinocytes were cultured in a 6-well plate for 24 hours in supplemented medium (KGM2 basic medium +SupplementMix, PromoCell) before being treated with various concentrations of Goldenrod in basic medium for 24 hours. The levels of VEGF and IL1α secreted by the keratinocytes in the culture media were determined by conventional sandwich ELISA assay (Quantikine, R&D Systems) according to the manufacturer's instructions. The level of secretion of the target protein was evaluated on at least two keratinocyte donors cultured in the presence or in the absence of the active ingredient. TGFβ and UVB, known to increase the level of VEGF and IL1α respectively, were used as positive controls.

The results presented are mean values of biological triplicates ±SD and are represented as a percentage relative to the control (which represents 100%).

Results:

The effect of Goldenrod was evaluated on the level of secretion of the keratinocytes of two specific biological targets:

IL1α, a well-known cytokine, involved in inflammation and ageing of the skin, and VEGF, a growth factor that stimulates micro-vascularization, and therefore improves the supply of nutrients and oxygen in the skin.

The Goldenrod extract inhibits the secretion of IL1α in a dose-dependent manner, with a maximum effect (54.1±14.6%) observed at a concentration of 0.0125%, and UVB stimulates IL1a (166±20.6%) relative to untreated cells (100%).

Evaluation of the keratinocytes treated with 0.1% of Goldenrod showed an increase in secretion of VEGF (205.4±20.3%) relative to untreated cells (100%). The results shown, obtained from one donor, are nevertheless representative of both donors tested.

It can therefore be concluded that Goldenrod is an effective ingredient for inhibiting the pro-inflammatory IL1α, whereas it stimulates VEGF and provides nutrition and oxygenation of the skin, which can combat ageing of the skin.

EXAMPLE 6

Determination of the Effect of Goldenrod on the Melanin Content in Normal Human Melanocytes in Culture Protocol:

Normal human epidermal melanocytes (PromoCell) obtained from two donors of high phototype were cultured in 96-well plates in supplemented medium (MGM2 basic medium +SupplementMix, PromoCell). The cells were incubated with growth medium containing various concentrations of Goldenrod (from 0.05 to 0.0625%) for 5 days. Afterwards, the culture medium was removed and the cells were washed with PBS (Gibco/Invitrogen). For extraction of the intracellular melanin, the cells were lysed in 1M NaOH, centrifuged at 12 000 revolutions per minute for 5 minutes, and the absorbance of the clear supernatants was measured at 490 nm. The melanin content was normalized relative to the total proteins per well at 595 nm (Biorad Protein Assay, Biorad).

The results are represented as a percentage of the untreated control, which is fixed at 100%.

Results:

Melanin is the chromophore of human skin, it is synthesized by the melanocytes of the epidermis and is mainly responsible for the colour of the skin. The possible effect of Goldenrod on the pigmentation of the skin was evaluated by chemical quantification of melanin in the treated and untreated cells.

Goldenrod at a concentration of 0.1% inhibits the melanin content of the melanocytes by 21.9±1.9% relative to the untreated cells.

It follows from this test that Goldenrod modulates the melanin content of the cultured normal human melanocytes and may therefore reduce the level of pigmentation of the skin (and therefore act as a depigmenting agent).

EXAMPLE 7

Determination of the Effect of Goldenrod on the Replicative Life of Primary Human Fibroblasts (HDF)

Protocol:

Primary human dermal fibroblasts (HDFs) were isolated from abdominoplasty of three different women donors aged 49, 58 and 65 years, supplied by Evercyte (Vienna, Austria). The cells were cultured at 37° C. and 7% $CO_2$ in DMEM medium F12/Ham (1:1) from Biochrome (Berlin, Germany) supplemented with 4 mM of L-glutamine and 10% of foetal calf serum. For the series passages, the cells were washed twice with 1×PBS and incubated with 0.1% of trypsin/0.02% of EDTA for 5-8 min. The cells that became detached were resuspended in medium containing Goldenrod to reach a final concentration of 0.00625% in the medium. The number of viable cells in 1 ml of cellular suspension was determined automatically using a Vi-CELL XR (Beckman Coulter).

Results:

Continuous culture by series passage of HDF in the presence of Goldenrod leads to a prolongation of the replicative life of the cells of 10.8% (data not shown).

EXAMPLE 8

Determination of the Effect of Continuous Treatment of HDF Cells with Goldenrod on the Transition of the Papillary Fibroblasts into Reticular Fibroblasts (PRT)

Protocol:

The HDFs were passaged in series as described in example 7 and were analysed for PRT by visual inspection of the morphology of the cells in the light microscope, and by quantification of the markers of the papillary phenotype (PDPN) and reticular phenotype (TGM2). Next, RNA was isolated using TRI Reagent (Sigma) according to the manufacturer's instructions. The RNA isolated was quantified with a NanoDrop ND-1000 spectrophotometer (Thermo Scientific) and 300 ng was transcribed to cDNA using the NCode VILO miRNA cDNA Synthesis Kit (Life Technologies). Real-time quantitative PCR (qPCR) was carried out in a RotorGene-6000 Thermocycler (Qiagen) using HOT FIREPol EvaGreen qPCR Mix Plus (NO ROX) from Solis BioDyne (Tartu, Estonia). Expression of mRNA was normalized relative to expression of GAPDH. The markers and primers used are as follows:

```
TGM2:
                                        (SEQ ID NO: 1)
fwd-GGCGAACCACCTGAACAAAC
and
                                        (SEQ ID NO: 2)
rev-AGGATGCAAAGAGGAACGCT, PDPN:
                                        (SEQ ID NO: 3)
fwd-GCATCGAGGATCTGCCAACT
and
                                        (SEQ ID NO: 4)
rev-CCCTTCAGCTCTTTAGGGCG, GAPDH (control):
                                        (SEQ ID NO: 5)
fwd-CGACCACTTTGTCAAGCTCA
and
                                        (SEQ ID NO: 6)
rev-TGTGAGGAGGGGAGATTCAG.
```

Results:

Continuous culture by series passages of HDF cells without the presence of Goldenrod leads to loss of the papillary morphology of the HDFs, whereas it is maintained in the presence of Goldenrod (data not shown).

This is confirmed by the fact that expression of the marker TGM2 (reticular marker) is lower, whereas expression of the marker PDPN (papillary marker) is higher, when the cells are cultured in the presence of Goldenrod, relative to the untreated cells (data not shown).

It is concluded that Goldenrod delays the transition from the papillary phenotype to the reticular phenotype of the HDFs.

Since young skin contains a higher number of papillary HDFs, this suggests once more that Goldenrod might help to maintain a young phenotype of the skin.

EXAMPLE 9

Determination of the Effect of Continuous Treatment of the HDF Cells with Goldenrod on Senescence Markers Protocol:

The HDFs were passaged in series as described in example 7, and were tested for senescence by labelling combined with β-galactosidase (β-SA-gal). Next, the cells were washed twice with 1×PBS and fixed for 10 min with 2% formaldehyde/0.2% glutaraldehyde. The cells were washed twice with 1×PBS, once with staining buffer (100 mM of citric acid/200 mM $Na_2HPO_4$, pH 6.0) and incubated with a staining solution (5 mM of potassium ferricyanide, 5 mM of potassium ferrocyanide, 2 mM of $MgCl_2$, 1 mg/ml of X-Gal, diluted in staining buffer) at 37° C. for 24 hours. For each well, 10 photographs were taken at random places of the well, and the images from one experiment were randomized and were counted blind by a single operator. In addition, qPCR was carried out as in example 9 using primers of the senescence markers (P21) and of young cells (SNEV), as follows:

$p21^{Cp1/WAF1}$ (CDKN1A): fwd-GGCGGCAGACCAGCAT-GACAGATT (SEQ ID NO:7) and rev-GCAGGGGGCG-GCCAGGGTAT (SEQ ID NO:8), $SNEV^{hPrp19/hPso4}$ (PRPF19): fwd-AACCACGGAGCG-CAAGAAG (SEQ ID NO:9) and rev-CGGGGGAAGCAGAAAACAC (SEQ ID NO:10), and were renormalized relative to the levels of mRNA of GAPDH.

Results:

Continuous culture by series passages of the HDFs in the presence of Goldenrod leads to a reduction in senescent cells of about 50% at all the times tested during series passage of the cells (data not shown). This is reflected in the drop in levels of mRNA of p21 as marker of the senescent cells and the increase in levels of mRNA of SNEV as marker of young cells (Voglauer et al., 2006).

This again confirms the activity of Goldenrod for delaying entry of the cells into replicative senescence.

EXAMPLE 10

Determination of the Effect of Acute Treatment with Goldenrod on the Senescence Marker in Prematurely Senescent HDFs Under the Effect of Stress (HDF SIPS)

Protocol:

The cells were seeded on day 0 at 3500 cells/cm² and treated on days 1-4 and 7-11 with 100 μM of $H_2O_2$ for 1 hour per day, and were then recovered in a normal growth medium. The quiescent control cells were seeded at the same density on day 0 and the medium was changed twice per week. Treatment with Goldenrod was carried out immediately after the last treatment with $H_2O_2$ on day 11.

The HDF SIPS were tested for senescence by labelling combined with O-galactosidase (SA-β-gal) as in example 10. qPCR was carried out as in example 10. In addition, after control of the quality of the RNA isolated with a Bioanalyzer 2100 (Agilent Technologies) using an RNA 6000 Nano Kit according to the manufacturer's instructions, next generation sequencing (NGS) was carried out by GATC Biotech (Constance, Germany) using an Illumina HiSeq 2500.

Results:

Acute treatment with Goldenrod decreases the SA-βGal positivity of the HDF SIPS by about 44% on day 4 and 80% on day 11 (data not shown). This is accompanied by a decrease in mRNA of p21, as well as positive regulation of mRNA of SNEV. In fact, the principle of principal component analysis (PCA) of the mRNA transcription profiles of the whole genome of quiescent cells and SIPS, treated with Goldenrod relative to the untreated cells, shows that Goldenrod has the effect of converting the profile of the transcriptome back to a quiescent cell profile. More precisely, transcription of mRNA of several factors of the pro-inflammatory senescence-associated secretory phenotype (SASP), which degrade the matrix, was reduced as illustrated by the examples of IL-11, CXCL8 (IL8), IFI30 (GILT), and CCL2.

Taken together, these results suggest that Goldenrod is capable of reconverting important functional changes that are produced during entry into cellular senescence, and which contribute to skin ageing.

EXAMPLE 11

Determination of the Effect of Acute Treatment with Goldenrod on the Long-Term Survival of HDF SIPS Cells Protocol:

The cells were seeded on day 0 at 3500 cells/cm$^2$ in T75 culture flasks and treated on days 1-4 and 7-11 with 100 µM of $H_2O_2$ for 1 hour per day, after which they were recovered in a normal growth medium. The quiescent control cells were seeded at the same density on day 0 and the medium was changed twice per week. The treatment with Goldenrod was carried out immediately after the last treatment with $H_2O_2$ on day 11. The cell count was determined as described in example 7.

Results:

Exposure of the HDF SIPS to Goldenrod for 4 days does not show a cytotoxic effect (data not shown). However, exposure to Goldenrod for more than 35 days results in activity of selective removal of the senescent cells (SESC) of the order of 30%, whereas the quiescent cells (controls) do not show a significant amount of cellular death. This indicates that long-term use of Goldenrod could reduce the number of senescent cells selectively.

EXAMPLE 12

Determination of the Effect of Acute Treatment with Goldenrod on the Long-term Survival of HDF SIPS Protocol:

Primary human keratinocytes derived from neonatal foreskin of individual donors (KC) were purchased from CellSystems (Troisdorf, Germany) and cultured in a KC growth medium (KGM, Clonetics, Gaithersburg, USA) supplemented with 0.1 ng/ml of recombinant human EGF, 5 µg/ml insulin, 0.5 µg/ml of hydrocortisone, 0.4% of bovine pituitary extract, 50 µg/ml of gentamicin and 50 ng/ml of amphotericin B. The RNA was isolated using the RNeasy 96 system (Invitrogen), and 900 ng of total RNA was reverse-transcribed with the iScript cDNA Synthesis Kit (Biorad). qPCR was performed using the LightCycler 480 and the LightCycler 480 SYBR Green I Master (Roche, Basle, Switzerland). Expression of the target genes was normalized relative to expression of β-2 microbulin. The sequences of the primers are as follows (5'-3'): B2Mf atgagtatgcctgccgtgtg (SEQ ID NO:11); B2Mr: caatccaaatgcggcatct (SEQ ID NO:12);

p16ink4Af: caacgcaccgaatagttacg (SEQ ID NO:13); p16ink4Ar: accagcgtgtccaggaag (SEQ ID NO:14);

MMP1_524f: ggtctctgagggtcaagcag (SEQ ID NO:15); MMP1_720r: ccgcaacacgatgtaagttg (SEQ ID NO:16).

The cells are seeded for the stress experiments on day 0 at 1500 cells/cm$^2$ and treated on days 2, 5 and 6 with Paraquat (PQ) (80 µm) for 24 hours. Treatment with Goldenrod was carried out on days 1 and 4 on untreated cells or cells treated with Paraquat.

Results:

The primary KCs were seeded in culture dishes, and treated either with PQ, or with Goldenrod, or with both. A total of 37500 cells per culture dish were seeded on day zero (0), and the cell counts were obtained at 3 and 7 days of treatment. The mean value of the number of cells counted for the control cells corrected for the cell division factor was:

for the untreated control cells, on D3: 720,000, on D7: 8,295,000;

for the cells treated with PQ, on D3: 405,000, on D7: 546,666;

for the cells treated with Goldenrod, on D3: 825,000, on D7: 8,400,000; and for the cells treated with PQ and Goldenrod, on D3: 510,000, on D7: 1,245,000 cells.

This shows that Goldenrod does not prevent the decrease in cellular proliferation under the effect of oxidative stress.

Treatment with Paraquat, a well-described inducer of cellular senescence, induces expression of MMP1 and p16INK4a.

P16INK4a is a marker gene of cellular senescence and its expression is regulated positively when the cell cycle has stopped.

MMP1 is a matrix metalloproteinase that is often secreted by senescent cells.

When Goldenrod was applied in addition to Paraquat, the expression levels of mRNA relative to the control gene (beta-2-microglobulin) were reduced. This shows that Goldenrod neutralizes the effect of Paraquat on arrest of the cell cycle and on the expression of genes associated with senescence.

EXAMPLE 13

Cosmetic Compositions

| 7A - oil/water cream gel emulsion | |
|---|---|
| INCI name | (% W/W) |
| Jojoba esters | 1-10 |
| Hydrogenated coconut oil | 1-10 |
| Moringa oil/hydrogenated moringa oil esters (FLORALIPIDS MORINGA BUTTER) | 1-10 |
| Butyrospermum parkii butter (LIPEX SHEASOFT) | 1-10 |
| Camellia kissi seed oil | 1-10 |
| Butyrospermum parkii butter extract (LIPEX SHEA TRIS) | 1-10 |
| Pentaerythrityl stearate/caprate/caprylate/adipate (SUPERMOL S-SO) | 0.5-5 |
| Cetyl ethylhexanoate | 1-5 |
| Octyl palmitate | 1-5 |
| Diisostearyl dimer dilinoleate (SCHERCEMOL DISD) | 1-10 |
| Octyldodecyl myristate | 1-5 |
| Hydrogenated lecithin | 0.1-5 |
| Cetearyl alcohol & cetearyl glucoside | 0.1-7 |
| Glyceryl stearate & PEG-100 stearate | 0.1-5 |

| 7A - oil/water cream gel emulsion | |
|---|---|
| INCI name | (% W/W) |
| CARBOMER | 0.01-5 |
| BIOSACCHARIDE GUM-1 | 1-10 |
| Methyl methacrylate crosspolymer (MAKIBEADS 150) | 0.1-10 |
| Sodium hyaluronate | 0.01-3 |
| Glycerin | 1-30 |
| Polyquaternium-51 | 1-10 |
| Adenosine | 0.1-0.5 |
| Nicotinamide | 0.1-5 |
| *Tremella fuciformis* polysaccharide | 0.1-5 |
| Palmitoyl Tripeptide-1 & Palmitoyl Tetrapeptide-7 | 1-5 |
| Secale cereale (Rye) Seed Extract | 1-5 |
| *Solidago virgaurea* subsp. *alpestris* extract | 0.01-10 |
| Ascorbyl glucoside | 0.001-5 |
| Glycols (Caprylyl Glycol and/or Pentylene Glycol and/or Butylene Glycol and/or propanediol) | 0.1-10 |
| Water | Qs 100 |

| 7b - oil/water cream emulsion | |
|---|---|
| INCI name | (% w/w) |
| Behenyl alcohol | 1-5 |
| Cetyl alcohol | 0.1-5 |
| Phenyl trimethicone | 1-5 |
| Dimethicone & Dimethicone/Vinyl Dimethicone Crosspolymer | 1-30 |
| Ectoin | 0.1-5 |
| PPG-2 myristyl ether propionate | 1-10 |
| Nanofine Titanium Dioxide | 1-20 |
| Zinc Dioxide | 1-20 |
| Diethylamino Hydroxybenzoyl Hexyl Benzoate (Uvinul A+) | 1-5 |
| Bis-Ethylhexyloxyphenol Methoxyphenyl Triazine (Tinosorb S) | 1-5 |
| (Tinosorb M) | 1-5 |
| Ethyl hexyl Methoxycinnamate | 1-7.5 |
| Polysilicone-11 | 1-5 |
| Silica | 1-5 |
| Polymethylsilsesquioxane | 1-5 |
| C20-22 alkyl phosphate & C20-22 alcohols | 0.5-5 |
| Glyceryl stearate & PEG-100 stearate | 0.5-5 |
| Sodium acrylate/sodium acryloyldimethyltaurate copolymer | 0.1-5 |
| Hydrogenated starch hydrolysate & maltooligosyl glucoside | 0.1-10 |
| Xanthan Gum | 0.01-2 |
| Agar | 0.1-5 |
| Adenosine | 0.1-0.5 |
| Nicotinamide | 0.1-5 |
| *Tremella fuciformis* polysaccharide | 0.1-5 |
| Palmitoyl Tripeptide-1 & Palmitoyl Tetrapeptide-7 | 1-5 |
| Secale cereale (Rye) Seed Extract | 1-5 |
| *Solidago virgaurea* subsp. *alpestris* extract | 0.01-10 |
| Ascorbyl glucoside | 0.001-5 |
| Water | Qs 100 |

These compositions may be applied on the skin every day, morning and/or evening.

The invention claimed is:

1. A cosmetic or dermatological composition comprising, in a cosmetically or pharmaceutically acceptable vehicle, an effective amount of an alcoholic extract of aerial parts of *Solidago virgaurea* subsp. *alpestris*,
   wherein said cosmetic or dermatological composition is in a form of an emulsion, and
   wherein said alcoholic extract of aerial parts of *Solidago virgaurea* subsp. *alpestris* is obtained by a method comprising the following steps:
   a) extracting a mixture of flowers, leaves and stems of *Solidago virgaurea* subsp. *alpestris*, previously dried and ground, with ethanol, at a temperature between 40° C. and 60° C. for 2 h to 5 h, to obtain an extracted mixture;
   b) incubating the extracted mixture obtained in a) for at least 12 h at a temperature between 2° C. and 6° C. to obtain an incubated mixture;
   c) filtering the incubated mixture obtained in b) to obtain a filtrate, bleaching the filtrate by adsorption on activated charcoal to obtain a decolored filtrate, filtering the decolored filtrate on a 20-μm membrane to obtain a final filtrate; and
   d) removing the ethanol from the final filtrate obtained, and then making a final dilution in 1,3-propanediol to obtain said alcoholic extract.

2. The cosmetic or dermatological composition according to claim 1, wherein the incubation in step b) is carried out for a length of time between 12 h and 30 h.

3. The cosmetic or dermatological composition according to claim 1, wherein said alcoholic extract of *Solidago virgaurea* subsp. *alpestris* acts as a depigmenting agent.

4. The cosmetic or dermatological composition according to claim 1, wherein said alcoholic extract of *Solidago virgaurea* subsp. *alpestris* acts as an antioxidant.

5. The cosmetic or dermatological composition according to claim 1, wherein said composition is suitable for application by the topical route.

6. A method for producing an alcoholic extract of *Solidago virgaurea* subsp. *Alpestris* comprising the steps of:
   a) extracting a mixture of flowers, leaves and stems of *Solidago virgaurea* subsp. *alpestris*, previously dried and ground, with ethanol at a temperature between 40° C. and 60° C. for 2 h to 5 h, to obtain an extracted mixture;
   b) incubating the extracted mixture obtained in a) for at least 12 h at a temperature between 2° C. and 6° C. to obtain an incubated mixture;
   c) filtering the incubated mixture obtained in b) to obtain a filtrate, bleaching the filtrate by adsorption on activated charcoal to obtain a decolored filtrate, filtering the decolored filtrate on a 20-μm membrane to obtain a final filtrate; and
   d) removing the ethanol from the final filtrate obtained, and then making a final dilution in 1,3-propanediol to obtain said alcoholic extract.

7. A method for attenuating changes to skin due to ageing, comprising topically applying an effective amount of the composition of claim 1 to the skin of a subject in need thereof.

* * * * *